United States Patent [19]

Lantzsch et al.

[11] Patent Number: 4,663,465
[45] Date of Patent: May 5, 1987

[54] PREPARATION OF 2,2-DIMETHYL-3-ARYL-CYCLO-PROPANECARBOXYLIC ACID AND ESTERS AND NEW INTERMEDIATES THEREFOR

[75] Inventors: Reinhard Lantzsch, Leverkusen; Dieter Arlt, Cologne; Manfred Jautelat, Burscheid, all of Fed. Rep. of Germany

[73] Assignee: Bayer Aktiengesellschaft, Leverkusen, Fed. Rep. of Germany

[21] Appl. No.: 805,502

[22] Filed: Dec. 4, 1985

Related U.S. Application Data

[62] Division of Ser. No. 683,540, Dec. 19, 1984, abandoned, which is a division of Ser. No. 496,718, May 20, 1983, abandoned.

[30] Foreign Application Priority Data

Jun. 2, 1982 [DE] Fed. Rep. of Germany ....... 3220732

[51] Int. Cl.[4] ................. C07D 327/00; C07D 409/00; C07D 307/02; C07D 307/48
[52] U.S. Cl. ......................................... 549/4; 549/60; 549/61; 549/62; 549/68; 549/79; 549/472; 549/474; 549/479; 549/480; 549/481; 549/499; 560/11; 560/19; 560/21; 560/36; 560/47; 560/59; 560/100; 560/102; 562/433; 562/435; 562/469; 562/490
[58] Field of Search ................... 549/66, 4, 60, 61, 62, 549/68, 79, 472, 474, 479, 480, 481, 499; 560/11, 19, 21, 36, 47, 59, 100, 102; 562/433, 435, 469, 490

[56] References Cited

FOREIGN PATENT DOCUMENTS 0043492 1/1982 European Pat. Off. .
0056154 7/1982 Fed. Rep. of Germany .
157792 12/1982 Fed. Rep. of Germany .

OTHER PUBLICATIONS

Jerry March, Advanced Organic Chem., Reactions, Mechanisms and Structure, pp. 315-318 and 341.
Arch. Pharm. (Weinheim) 313, 795-799 (1980), 3-Aryl-2-Hydroxy-2,2-Dimethyl-. . . Tetrahydropyran-2,4-Dione.

Bull. Chem. Soc. 1962, p. 23, 3) Preparation du cctol (XIV) Lil.5) Tetrahedron 40, pp. 1273-1274.

Primary Examiner—Alan Siegel
Attorney, Agent, or Firm—Sprung, Horn, Kramer & Woods

[57] ABSTRACT 2,2-Dimethyl-3-arylcyclopropanecarboxylic acids and esters, suitable as insecticide intermediates, of the formula

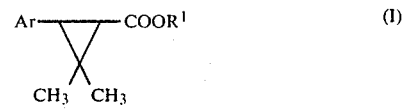

in which
Ar is naphthyl or substituted furyl, thienyl or phenyl, and
$R^1$ is hydrogen or alkyl, are produced by subjecting

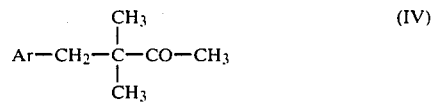

to radical polymerization to produce

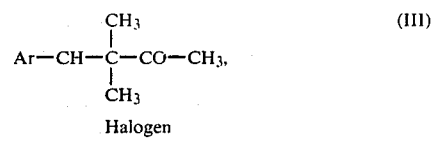

reacting that with chlorine or bromine to produce

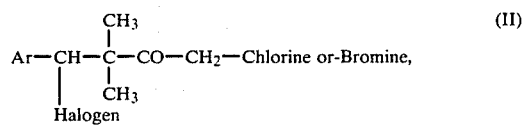

and reacting that with an alkali metal or alkaline earth metal hydroxide or carbonate. Various intermediates II and III are new.

2 Claims, No Drawings

PREPARATION OF 2,2-DIMETHYL-3-ARYL-CYCLOPROPANECARBOXYLIC ACID AND ESTERS AND NEW INTERMEDIATES THEREFOR

This is a division of application Ser. No. 683,540, filed Dec. 19, 1984, now abandoned, which is a division of Ser. No. 496,718, filed May 20, 1983 now abandoned.

The present invention relates to a new process for the preparation of 2,2-dimethyl-3-arylcyclopropanecarboxylic acids (carboxylic esters), most of which are known and which can be used as intermediate products for the preparation of 2,2-dimethyl-3-arylcyclopropanecarboxylic esters having insecticidal activity, new 1-aryl-1,4 dihalogeno-2,2-dimethyl-3-butanones as intermediate products for this purpose and a process for their preparation, together with new 1-aryl-1-halogeno-2,2-dimethyl-3-butanones as intermediate products for this purpose and a process for their preparation.

It has been disclosed that certain 2,2-dimethyl-3-arylcyclopropanecarboxylic acids are obtained when corresponding 1-aryl-2-methylpropenes are reacted with diazoacetic esters in the presence of catalysts, and the 2,2-dimethyl-3-arylcyclopropanecarboxylic esters formed in this reaction are hydrolyzed (compare: Coll. Czech. Chem. Commun. 25 (1960), 1815). However, this method of synthesis has only a limited range of use. The yields depend greatly on the nature of the aryl radicals and are unsatisfactory in many cases; on reacting 1-thienyl-2-methylpropenes with diazoacetic esters, only decomposition products are obtained. In addition, the use of diazoacetic esters is associated with the known safety risks. Furthermore, the starting materials can mostly only be prepared with difficulty.

Moreover, the synthesis of ethyl 2,2-dimethyl-3-phenylcyclopropanecarboxylic via 4-methyl-3-phenyl-γ-valerolacetone has been disclosed (compare Bull. Soc. Chim. France 1961, 1857). However, this route demands a number of precursors, some of which are relatively complicated, and provides only a low yield overall.

2,2-dimethyl-3-phenylcyclopropanecarboxylic esters are also obtained by catalytic hydrogenation of 2,2-dimethyl-3-γ-phenylcyclopropenecarboxylic esters (compare: Chem. Ber. 111 (1978), 3879). However, the synthesis of the 2,2-dimethyl-3-phenylcyclopropenecarboxylic esters required as starting materials takes place via several steps, some of which are very difficult.

Furthermore, 2,2-dimethyl-3-arylcyclopropanecarboxylic esters can also be prepared by reaction of cinnamic esters with triphenylisopropylphosphonium iodide in the presence of strong bases, such as, for example, butyllithium (compare: Japanese Patent Specification No. 8,105,435). However, this process is industrially elaborate and costly.

The present invention relates to:

1. a process for the preparation of 2,2-dimethyl-3-arylcyclopropanecarboxylic acids (carboxylic esters) of the formula (I)

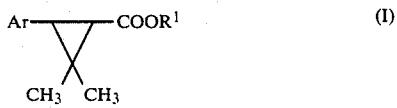

in which

Ar represents naphthyl or the radical

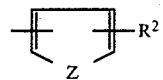

wherein

Z represents oxygen, sulphur or 1,2-ethenediyl (—CH=CH—), $R^1$ represents H or $C_1$-$C_4$-alkyl and $R^2$ represents hydrogen, halogen, cyano, nitro, trialkylsilyl or a radical, which is optionally substituted by halogen, from the series comprising alkyl, cycloalkyl, alkenyl, alkoxy, alkenedioxy, alkylthio, alkylsulphinyl, alkylsulphonyl, dialkylamino, phenyl and phenoxy, characterized in that 1-aryl-1,4-dihalogeno-2,2-dimethyl-3-butanones of the formula (II)

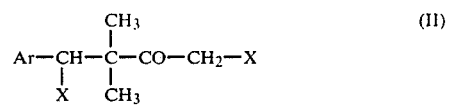

in which

Ar has the abovementioned meaning and

X represents chlorine or bromine, are reacted with bases from the series comrising the alkali metal and alkaline earth metal hydroxides, alcoholates and carbonates, in the presence of water and organic solvents, where appropriate in the presence of catalysts, at temperatures between −20° C. and +100° C.;

2. new 1-aryl-1,4-dihalogeno-2,2-dimethyl-3-butanones of the formula (II)

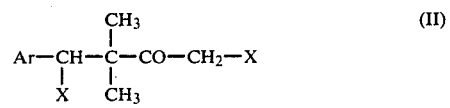

in which

X represents chlorine or bromine and

Ar represents naphthyl or the radical

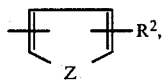

wherein

Z represents oxygen, sulphur or 1,2-ethenediyl (—CH=CH—) and $R^2$ represents hydrogen, halogen, cyano, nitro, trialkylsilyl or a radical, which is optionally substituted by halogen, from the series comprising alkyl, cycloalkyl, alkenyl, alkoxy, alkylenedioxy, alkylthio, alkylsulphinyl, alkylsulphonyl, dialkylamino, phenyl and phenoxy;

3. a process for the preparation of the new 1-aryl-1,4-dihalogeno-2,2-dimethyl-3-butanones of the formula (II) above, characterized in that 1-aryl-1-halogeno-2,2-dimethyl-3-butanones of the formula (III)

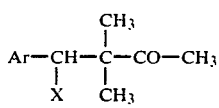

in which
Ar and X have the abovementioned meaning, are reacted with halogens (chlorine and bromine) in the presence of inert diluents at temperatures between $-30°$ C. and $+50°$ C.;

4. new 1-aryl-1-halogeno-2,2-dimethyl-3-butanones of the formula (IIIa)

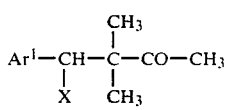

in which
X represents chlorine or bromine and
$Ar^1$ represents naphthyl or the radical

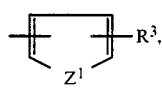

wherein
$Z^1$ represents oxygen or 1,2-ethenediyl (—C=CH—) and
$R^3$ represents cyano, nitro, trialkylsilyl or a radical, which is optionally substituted by halogen, from the series comprising cycloalkyl, alkenyl, alkylenedioxy, alkylthio, alkylsulphinyl, alkylsulphonyl, dialylamino, phenyl and phenoxy, or represents alkyl which is different from methyl, or represents alkoxy which is different from methoxy, or represents halogenoalkyl or halogenoalkoxy, or, in the case where X represents bromine, also represents hydrogen, halogen, methyl or methoxy;

5. a process for the preparation of the new 1-aryl-1-halogeno-2,2-dimethyl-3-butanones of the formula (IIIa) (above), characterized in that 1-aryl-2,2-dimethyl-3-butanones of the formula (IV)

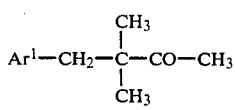

in which
$Ar^1$ has the abovementioned meaning, are subjected to radical halogenation, where appropriate in the presence of an inert diluent and in the presence of a catalyst at temperatures between 40° C. and 120° C.

It is surprising that 2,2-dimethyl-3-arylcyclopropanecarboxylic acids (carboxylic esters) can be prepared in good yields starting from 1-aryl-2,2-dimethyl-3-butanones via the corresponding 1-halogeno- and 1,4-dihalogeno-derivatives, since it is known from the literature that 1-aryl-1-halogeno-2,2-dimethyl-3-butanones react with alkali metal hydroxides in aqueous-organic solution with substitution of the halogen by a hydroxyl group (compare: Arch. Pharm. 313 (1980), 795). Equally, it could not have been foreseen that, on the one hand, radical halogenation of the 1-aryl-2,2-dimethyl-3-butanones in the 1-position (on the methylene group) is possible virtually without competing attack of the halogenating agent in the 4-position (on the methyl group) and, on the other hand, the reaction of the 1-aryl-1-halogeno-2,2-dimethyl-3-butanones formed in this reaction with elementary halogen takes place selectively on the methyl group with formation of the 1-aryl-1,4-dihalogeno-2,2-dimethyl-3-butanones.

The process according to the invention has a number of advantages. Thus, reasonably priced or easily prepared reactants and solvents can be employed without special pretreatments. The individual process steps can be carried out without particular elaboration and, in general, the products are obtained in high yields.

If, for example, 1-(4-fluorophenyl)-1,4-dichloro-2,2-dimethyl-3-butanone and potassium hydroxide are used as starting components in the process set out above under (1) for the preparation of 2,2-dimethyl-3-arylcyclopropanecarboxylic acids (carboxylic esters), then the process according to the invention can be outlined, using this example, by the following scheme:

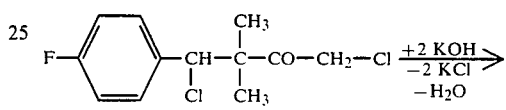

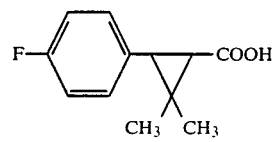

Apart from water, organic solvents are employed to carry out the process according to the invention set out above under (1). Those solvents suitable are preferably, on the one hand, polar and miscible with water, such as, for example, acetone, methyl ethyl ketone, methyl isobutyl ketone, acetonitrile, tetrahydrofuran, dioxane and 1,2-dimethoxyethane, or, on the other hand, solvents which are virtually immiscible with water from the series of optionally halogenated hydrocarbons, such as, for example, hexane, cyclohexane, heptane, petroleum ether, ligroin, methylene chloride, chloroform, benzene, toluene and xylene.

In addition, alcohols can also be employed as solvents, such as, for example, methanol, ethanol, isopropanol and tert.-butanol.

When using solvents which are virtually immiscible with water, phase transfer catalysts from the series of tetraalkyl- or trialkylaralkyl-ammonium salts, such as, for example, tetrabutylammonium bromide or triethylbenzylammonium chloride are preferably employed.

The bases employed in the process according to the invention are alkali metal or alkaline earth metal hydroxides, such as, for example, sodium, potassium, magnesium and calcium hydroxide, alkali metal or alkaline earth metal carbonates, such as, for example, sodium, potassium, magnesium and calcium carbonate or alkali metal alcoholates, such as, for example, sodium or potassium methylate, sodium or potassium ethylate, sodium isopropylate and potassium tert.-butylate.

For the preparation of the acids, alkali metal hydroxides, such as, for example, sodium hydroxide or potassium hydroxide are preferably employed.

For the preparation of the esters, the alkali metal alcoholates, such as, for example, sodium methylate, sodium ethylate, sodium isopropylate and potassium tert.-butylate are preferably employed. The corresponding alcohols are then preferably used as the solvent.

In carrying out the process according to the invention, the reaction temperatures are generally maintained between $-20°$ C. and $+150°$ C., preferably between $+10°$ C. and $+100°$ C.

The process according to the invention is generally carried out under normal pressure.

In order to carry out the process according to the invention, in general, 2 to 15 mol-equivalents, preferably 2 to 10 mol-equivalents of a base are employed per 1 mol of 1-aryl-1,4-dihalogeno-2,2-dimethyl-3-butanone. In a preferred embodiment of the process according to the invention, the aqueous solution of the base, if appropriate diluted with an organic solvent, is initially introduced and the 1-aryl-1,4-dihalogeno-2,2-dimethyl-3-butanone of the formula (II), if appropriate dissolved in an organic solvent, and, if appropriate, a catalyst, are added to the former. The reaction mixture is stirred until the reaction has ended and worked up in a conventional manner, for example by acidification and extraction with methylene chloride. The product of the formula (I) is obtained as a crystalline residue after distilling off the organic extracting agent.

The new 1-aryl-1,4-dihalogeno-2,2-dimethyl-3-butanones to be used as intermediate products in the process according to the invention are generally defined by the formula (II) above under (2).

In this formula:

X preferably represents chlorine or bromine and

Ar preferably represents naphthyl or the radical

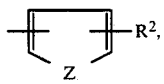

wherein

Z represents oxygen, sulphur or 1,2-ethenediyl ($-CH=CH-$) and $R^2$ represents hydrogen, fluorine, chlorine, bromine, cyano, nitro, trimethylsilyl or a radical, which is optionally substituted by chlorine and/or fluorine, from the series comprising $C_1$-$C_6$-alkyl, $C_3$-$C_6$-cycloalkyl, $C_2$-$C_6$-alkenyl, $C_1$-$C_4$-alkoxy, $C_1$-$C_2$-alkylenedioxy, $C_1$-$C_4$-alkylthio, $C_1$-$C_4$-alkylsulphinyl, $C_1$-$C_4$-alkylsulphonyl, di-$C_1$-$C_4$-alkylamino, phenyl and phenoxy.

The compounds of the formula (II) are particularly preferred, in which

X represents chlorine or bromine and

Ar represents phenyl which is optionally substituted in the meta and/or para position by fluorine, chlorine, bromine, $C_1$-$C_4$-alkyl, trifluoromethyl, methoxy, trifluoromethoxy, methylenedioxy or difluoromethylenedioxy.

Examples of the new compounds of the formula (II) which may be mentioned are: 1-phenyl-, 1-(4-fluorophenyl)-, 1-(4-chlorophenyl)-, 1-(4-methylphenyl)-, 1-(4-tert.-butylphenyl)-, 1-(4-trifluoromethylphenyl)-, 1-(4-methoxyphenyl)- and 1-(4-trifluoromethoxyphenyl)-1,4-dichloro-2,2-dimethyl-3-butanone and 1-phenyl-, 1-(4-fluorophenyl)-, 1-(4-chlorophenyl)-, 1-(4-methylphenyl)-, 1-(4-tert.-butylphenyl)-, 1-(4-trifluoromethylphenyl)-, 1-(4-methoxyphenyl)- and 1-(4-trifluoromethoxy-phenyl)-1,4-dibromo-2,2-dimethyl-3-butanone.

If, for example, 1-(4-fluorophenyl)-1-chloro-2,2-dimethyl-3-butanone and chlorine are used as starting materials for the preparation of the new 1-aryl-1,4-dihalogeno-2,2-dimethyl-3-butanones in the process set out under (3), then the reaction between them according to the invention can be outlined by the following scheme:

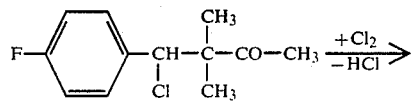

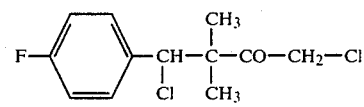

The process according to the invention set out under (3) is carried out using inert diluents. Suitable as such are preferably halogenated hydrocarbons, such as, for example, methylene chloride, chloroform, dichlorodifluoromethane, tetrachloromethane and ethylene chloride and, where appropriate, also carboxylic acids, such as, for example, acetic acid.

The reaction is carried out at temperatures between $-30°$ C. and $+50°$ C., preferably at $0°$ C. to $+20°$ C. and, in general, under normal pressure.

In general, 0.8 to 1.2 mols, preferably 0.9 to 1 mol, of chlorine or bromine is employed per 1 mol of 1-aryl-1-halogeno-2,2-dimethyl-3-butanone of the formula (III).

In a preferred embodiment of the process set out under (3), a solution of the 1-aryl-1-halogeno-2,2-dimethyl-3-butanone is initially introduced and the halogen is metered in slowly in the form of a gas or in solution. After the reaction has ended, the product of the formula (II) is isolated by distilling off the solvent.

The 1-aryl-1-halogeno-2,2-dimethyl-3-butanones necessary as intermediate products are generally defined by the formula (III) above under (3). In formula (III), the radicals Ar and X preferably or particularly preferably have the same meanings as are given in the definition of the corresponding radicals Ar and X in formula (II) as being "preferred" or "particularly preferred" respectively.

Examples of compounds of the formula (III) which are already known, compare: Arch. Pharm. 308 (1975), 422, and which may be mentioned are: 1-(4-methylphenyl, 1-(4-methoxyphenyl)- and 1-(2-thienyl)-1-chloro-2,2-dimethyl-3-butanone.

The new 1-aryl-1-halogeno-2,2-dimethyl-3-butanones are defined by the formula (IIIa) above under (4). In this formula X preferably represents chlorine or bromine and $Ar^1$ preferably represents naphthyl or the radical

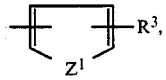

wherein $Z^1$ represents oxygen or 1,2-ethenediyl ($-CH=CH-$) and $R^3$ represents fluorine, bromine, cyano, nitro or trimethylsilyl or represents methyl or methoxy radicals substituted by fluorine and/or chlorine or represents radicals, which are optionally substituted by fluorine and/or chlorine, from the series comprising $C_2$-$C_6$-alkyl, $C_3$-$C_6$-cycloalkyl, $C_2$-$C_6$-alkenyl, $C_2$-$C_4$-alkoxy, $C_1$-$C_2$-alklenedioxy, $C_1$-$C_4$-alkylthio, $C_1$-$C_4$-alkylsulphinyl, $C_1$-$C_4$-alkylsulphonyl, di-$C_1$-$C_4$-alkylamino, phenyl and phenoxy, or, for the case where X represents bromine, also represents hydrogen, chlorine, methyl or methoxy.

Those compounds of the formula (IIIa) are particularly preferred in which

X represents chlorine or bromine and $Ar^1$ represents phenyl which is substituted in the meta and/or para position by fluorine, bromine, $C_2$-$C_4$-alkyl, trifluoromethyl, trifluoromethoxy, methylenedioxy or difluoromethylenedioxy and, for the case where X represents bromine, also represents phenyl or represents phenyl substituted in the meta and/or para position by methyl, methoxy or chlorine.

Examples of the new compounds of the formula (IIIa) which may be mentioned are: 1-(4-fluorophenyl)-, 1-(4-tert.-butylphenyl)-, 1-(4-trifluoromethylphenyl)- and 1-(4-trifluoromethoxyphenyl)-1-chloro-2,2-dimethyl-3-butanone and 1-phenyl-, 1-(4-fluorophenyl)-, 1-(4-chlorophenyl)-, 1-(4-methylphenyl)-, 1-(4-tert.-butylphenyl)-, 1-(4-trifluoromethylphenyl)-, 1-(4-methoxyphenyl)- and 1-(4-trifluoromethoxyphenyl)-1-bromo-2,2-dimethyl-3-butanone.

If, for example, 1-(4-fluorophenyl)-2,2-dimethyl-3-butanone and N-chlorosuccinimide are used as starting materials for the preparation of the new 1-aryl-1-halogeno-2,2-dimethyl-3-butanones of the formula (IIIa) by the process set out above under (5), then the reaction between them according to the invention can be outlined by the following scheme:

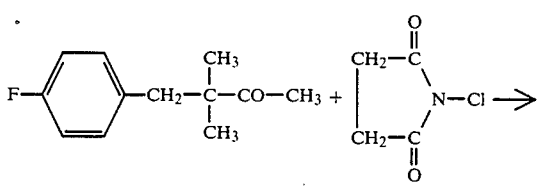

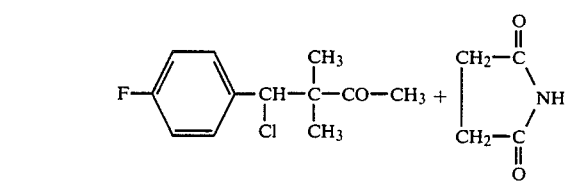

The process according to the invention set out under (5) is preferably carried out using inert diluents. Suitable as such are preferably halogenated hydrocarbons, such as, for example, methylene chloride, chloroform, dichlorodifluoromethane, tetrachloromethane and ethylene chloride.

Compounds providing free radicals, such as, for example, azobisisobutyronitrile, benzoyl peroxide or di-tert.-butyl peroxide are preferably used as catalysts.

The reaction is generally carried out at temperatures between 40° C. and 120° C., preferably at 60° C. to 100° C. and generally under normal pressure or moderately raised pressure at about 10 bar.

In general, between 1 and 2 mol-equivalents, preferably 1 to 1.2 mol-equivalents of a halogenating agent are employed per 1 mol of 1-aryl-2,2-dimethyl-3-butanone of the formula (IV). Suitable halogenating agents are N-halogenosuccinimides, such as, for example, N-bromosuccinimide or N-chlorosuccinimide.

In order to carry out the process set out under (5) for the preparation of the new 1-aryl-1-halogeno-2,2-dimethyl-3-butanones of the formula (IIIa), corresponding 1-aryl-2,2-dimethyl-3-butanones, halogenating agents and catalysts are heated in suitable diluents until reaction has ended and the products of the formula (IIIa) are isolated by distillation under high vacuum.

The process set out under (5) is also considerably more suitable for the preparation of known compounds of the formula (III), such as, for example, 1-(4-chlorophenyl)-1-chloro-2,2-dimethyl-3-butanone, than the method of synthesis known from the literature (compare Arch. Pharm. 308 (1975), 422).

The 1-aryl-2,2-dimethyl-3-butanones required as intermediate products are generally defined by formula (IV) above under (5). In formula (IV), the radicals $Ar^1$ and X preferably or particularly preferably have the same meanings as are given above in the definition of the corresponding radicals $Ar^1$ and X in formula (IIIa) as being "preferred" or "particularly preferred" respectively.

Examples of the formula (IV) which may be mentioned are: 1-phenyl-, 1-(4-fluorophenyl)-, 1-(4-chlorophenyl)-, 1-(4-methylphenyl)-, 1-(4-tert.-butylphenyl)-, 1-(4-trifluoromethylphenyl)-, 1-(4-methoxyphenyl)- and 1-(4-trifluoromethoxyphenyl)-2,2-dimethyl-3-butanone.

Some of the 1-aryl-2,2-dimethyl-3-butanones of the formula (IV) have not yet been described in the literature. A patent application serial no which has not been prepublished (compare 802,076 filed Nov. 26, 1986, Le A 21 642) deals with a process for their preparation.

According to this, the 1-aryl-2,2-dimethyl-3-butanones of the formula (IV) are obtained when arylmethyl halides of the formula (V)

$$Ar^1—CH_2—X^1 \qquad (V)$$

in which $Ar^1$ has the abovementioned meaning and $X^1$ represents halogen, preferably chlorine, are reacted with methyl isopropyl ketone in the presence of a base, such as, for example, potassium hydroxide, in the presence of a diluent, such as, for example, toluene, and in the presence of a phase transfer catalyst, such as, for example, tetrabutylammonium bromide, at temperatures between 20° C. and 130° C. and, after filtering and washing the reaction mixture, the products of the formula (IV) are isolated by distillation under high vacuum.

The 2,2-dimethyl-3-arylcyclopropanecarboxylic acids of the formula (I) to be prepared by the process according to the invention can be used as intermediate products for the preparation of 2,2-dimethyl-3-arylcyclopropanecarboxylic esters having insecticidal activity (compare Coll. Czech. Chem. Commun. 25 (1960), 1815).

PREPARATION EXAMPLES

EXAMPLE 1

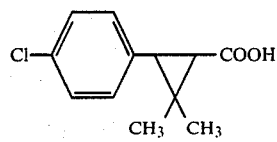

45 g (0.12 mol) of 1-(4-chlorophenyl)-1,4-dibromo-2,2-dimethyl-3-butanone are added dropwise at 20° C. to a solution of 48.8 g (1.2 mols) of sodium hydroxide in 400 ml of water and 100 ml of dioxane. The reaction mixture is stirred for 20 hours and extracted with methylene chloride. After acidification of the aqueous phase, it is again extracted with methylene chloride. After distilling off the solvent from the combined extraction solutions, 25.8 g (94% of theory) of cis/trans-2,2-dimethyl-3-(4-chlorophenyl)cyclopropanecarboxylic acid of melting point 115° C. are obtained.

The pure trans-2,2-dimethyl-3-(4-chlorophenyl)cyclopropanecarboxylic acid of melting point 137° C. is obtained by recrystallization from diisopropyl ether.

EXAMPLE 2

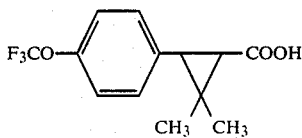

5.0 g of 1,4-dibromo-1-(4-trifluoromethoxyphenyl)-2,2-dimethyl-3-butanone (for preparation of the crude product, see Example 4, purity about 85%) are added at 20° C. to a solution of 4 g of sodium hydroxide in 40 ml of water and 20 ml of dioxane. The reaction mixture is stirred for 15 hours and extracted with methylene chloride. The aqueous phase is acidified and again extracted with methylene chloride. After distilling off the solvent from the combined extraction solutions, 2.4 g of 2,2-dimethyl-3-(4-trifluoromethoxyphenyl)cyclopropanecarboxylic acid of melting point 86° C. are obtained.

EXAMPLE 3

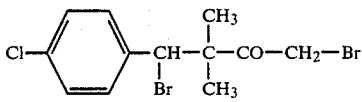

54 g (0.187 mol) of 1-(4-chlorophenyl)-1-bromo-2,2-dimethyl-3-butanone are dissolved in 500 ml of chloroform. A solution of 29.9 g of (0.187 mol) of bromine in 100 ml of chloroform is added dropwise at an internal temperature of 5° C. The reaction mixture is then allowed to come to room temperature while stirring and the solvent is distilled off under reduced pressure. 66 g of an oil, which consists principally of 1-(4-chlorophenyl)-1,4-dibromo-2,2-dimethyl-3-butanone, are obtained. $^1$H NMR (CDCl$_3$): $\delta = 1.2$ and 1.55 ppm (6H, 2 CH$_3$); 4.15 ppm (CH$_2$); 5.35 ppm (CH); 7.35 ppm (4H, Ar—H).

EXAMPLE 4

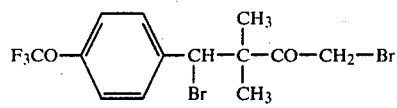

1,4-Dibromo-1-(4-trifluoromethoxyphenyl)-2,2-dimethyl-3-butanone were obtained as a crude product in analogy to Example (3) and reacted further without further purification (compare Example (2)).

EXAMPLE 5

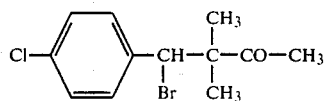

50 g (0.237 mol) of 1-(4-chlorophenyl)-2,2-dimethyl-3-butanone are dissolved in 500 ml of tetrachloromethane, and 44.5 g (0.25 mol) of N-bromosuccinimide and 0.5 g of azobisisobutyronitrile are added. The reaction mixture is heated to boiling under reflux until solid material no longer sinks to the bottom on switching off the stirrer. After cooling down, the succinimide is filtered off with suction, the solvent is distilled off from the filtrate under waterpump vacuum and the residue is distilled under high vacuum.

56.3 g (82% of theory) of 1-(4-chlorophenyl)-1-bromo-2,2-dimethyl-3-butanone of boiling point 112°–118° C./0.2 mbar are obtained.

EXAMPLE 6

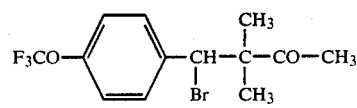

1-(4-Trifluoromethoxyphenyl)-1-bromo-2,2-dimethyl-3-butanone were obtained in analogy to Example 5. Boiling point 95°–104° C./0.2 mbar; n$_D^{20}$: 1.502.

EXAMPLE 7

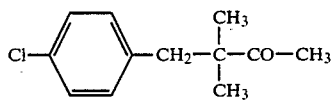

254 g (4 mols) of powdered technical potassium hydroxide (88% pure) are suspended in 1 liter of toluene. To this are slowly added 40 g of tetrabutylammonium bromide and a mixture of 644 g (4 mols) of 4-chlorobenzyl chloride and 430 g (5 mols) of methyl isopropyl ketone at 85° C. The reaction mixture is stirred a further 3 hours at 85° C. and, after cooling down, it is filtered and the filtrate is washed to neutrality. 732.5 g (87% of theory) of 1-(4-chlorophenyl)-2,2-dimethyl-3-butanone of boiling point 87°–90° C./0.05 mbar are obtained by fractional distillation under high vacuum.

EXAMPLE 8

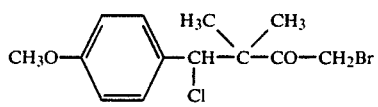

20 g (0.083 mol) of 2,2-dimethyl-1-chloro-1-(4-methoxyphenyl)-3-butanone (Archiv der Pharmazie 308, 422) are dissolved in 150 ml of chloroform, and 13.28 g (0.083 mol) of bromine are added dropwise at room temperature. The mixture is stirred at 20°–25° C. for a further 2 hours and the solvent is distilled off. 26.5 g of an oil remain, which consists principally of 4-bromo-2,2-dimethyl-1-chloro-1-(4-methoxyphenyl)-3-butanone and is directly reacted further.

EXAMPLE 9

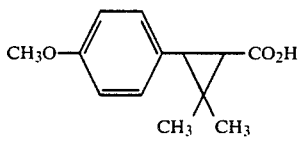

100 ml of acetone are added to a solution of 35.3 g (0.882 mol) of sodium hydroxide in 317 ml of water. Then, at 25° C., 26.5 g (0.083 mol) of 4-bromo-2,2-dimethyl-1-chloro-1-(4-methoxyphenyl)-3-butanone are added dropwise. The mixture is stirred at 25° C. for a further 12 hours, poured onto water and extracted with methylene chloride. The aqueous phase is acidified and extracted again. 12.6 g (69% of theory) of 2,2-dimethyl-3-(4-methoxyphenyl)cyclopropanecarboxylic acid of melting point 115° C. are obtained.

It will be appreciated that the instant specification and examples are set forth by way of illustration and not limitation, and that various modifications and changes may be made without departing from the spirit and scope of the present invention.

We claim:

1. A process for the preparation of a 2,2-dimethyl-3-arylcyclopropanecarboxylic acid or ester of the formula

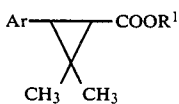

in which
$R^1$ is hydrogen or $C_1$-$C_4$-alkyl,
Ar is naphthyl or the radical

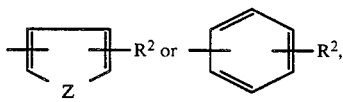

Z is oxygen or sulphur, and
$R^2$ is hydrogen, halogen, cyano, nitro, trialkylsilyl, a radical from the series comprising alkyl, cycloalkyl, alkenyl, alkoxy, alkylenedioxy, alkylthio, alkylsulphinyl, alkylsulphonyl, dialkylamino, phenyl and phenoxy, or a radical from the series comprising alkyl substituted by halogen, cycloalkyl substituted by halogen, alkenyl substituted by halogen, alkoxy substituted by halogen, alkylenedioxy substituted by halogen, alkylthio substituted by halogen, alkylsulphinyl substituted by halogen, alkylsulphonyl substituted by halogen, dialkylamino substituted by halogen, phenyl substituted by halogen and phenoxy substituted by halogen, comprising reacting a 1-aryl-1,4-dihalogeno-2,2-dimethyl-3-butanone of the formula

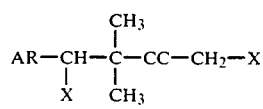

in which
Ar is naphthyl or the radical

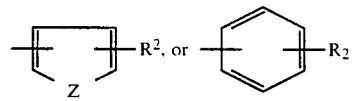

X is chlorine or bromine, with a based selected from the group comprising alkali metal and alkaline earth metal hydroxides, alcoholates and carbonates, in the presence of water and an organic solvent, at a temperature between about $-20\pm C.$ and $+150\pm C.$ 2. A process according to claim 1, in which
Ar is phenyl or phenyl which is substituted in the meta and/or para position by fluorine, chlorine, bromine, $C_1$-$C_4$-alkyl, trifluoromethyl, methoxy, trifluoromethyoxy, methylenedioxy or difluoromethylenedioxy, and
$R^2$ is hydrogen, fluorine, chlorine, bromine, cyano, nitro, trimethylsilyl or a radical from the series comprising $C_1$-$C_6$-alkyl, $C_3$-$C_6$-cycloalkyl, $C_2$-$C_6$-alkenyl, $C_1$-$C_4$-alkoxy, $C_1$-$C_2$-alkylenedioxy, $C_1$-$C_4$-alkylthio, $C_1$-$C_4$-alkylsulphinyl, $C_1$-$C_4$-alkylsulphonyl, di-$C_1$-$C_4$-alkylamino, phenyl and phenoxy or a radical from the series comprising $C_1$-$C_6$-alkyl substituted by chlorine and/or fluorine, $C_3$-$C_6$-cycloalkyl substituted by chlorine and/or fluorine $C_2$-$C_6$-alkenyl substituted by chlorine and/or fluorine, $C_1$-$C_4$-alkoxy substituted by chlorine and/or fluorine, $C_1$-$C_2$-alkylenedioxy substituted by chlorine and/or fluorine, $C_1$-$C_4$-alkylthio substituted by chlorine $C_1$-$C_4$-alkylsulphinyl substituted by chlorine and/or fluorine, $C_1$-$C_4$-alkylsulphonyl substituted by chlorine and/or fluorine, di-$C_1$-$C_4$-alkylamino substituted by chlorine and/or fluorine, phenyl substituted by chlorine and/or fluorine, and phenoxy substituted by chlorine and/or fluorine.

* * * * *